United States Patent [19]

Campbell

[11] 4,064,569
[45] Dec. 27, 1977

[54] ARTIFICIAL POLYCENTRIC KNEE JOINT
[76] Inventor: Harry E. Campbell, 15902 Parthenia, Sepulveda, Calif. 91343
[21] Appl. No.: 725,862
[22] Filed: Sept. 23, 1976
[51] Int. Cl.$^2$ .......................... A61F 1/04; A61F 1/08
[52] U.S. Cl. ............................................. 3/26; 3/21
[58] Field of Search ........................................ 3/22–29, 3/2

[56] References Cited
U.S. PATENT DOCUMENTS 3,820,169   6/1974   Long et al. .......................... 3/22
4,005,496   2/1977   Wilkes ................................. 3/22 X

FOREIGN PATENT DOCUMENTS 810,752   1/1937   France ................................. 3/22
441,658   11/1948   Italy .................................... 3/22

Primary Examiner—Ronald L. Frinks
Attorney, Agent, or Firm—Francis X. LoJacono, Sr.

[57] ABSTRACT

An artificial polycentric knee-joint mechanism comprising a four-bar linkage arranged to provide a motion similar to a normal knee having positive stability during ambulation. The four bars include a knee-mounting block mounted to the stump-receiving socket member and a lower linkage support-carriage member affixed to the lower limb component, the mounting block and linkage support being operably interconnected by side bar links, one of which is tension controlled. Also, included is a braking control to insure normal swing phase movement of the artificial leg and a shock absorbing device to prevent excess terminal impact when the lower limb returns to the extended position of the leg prosthesis.

10 Claims, 8 Drawing Figures

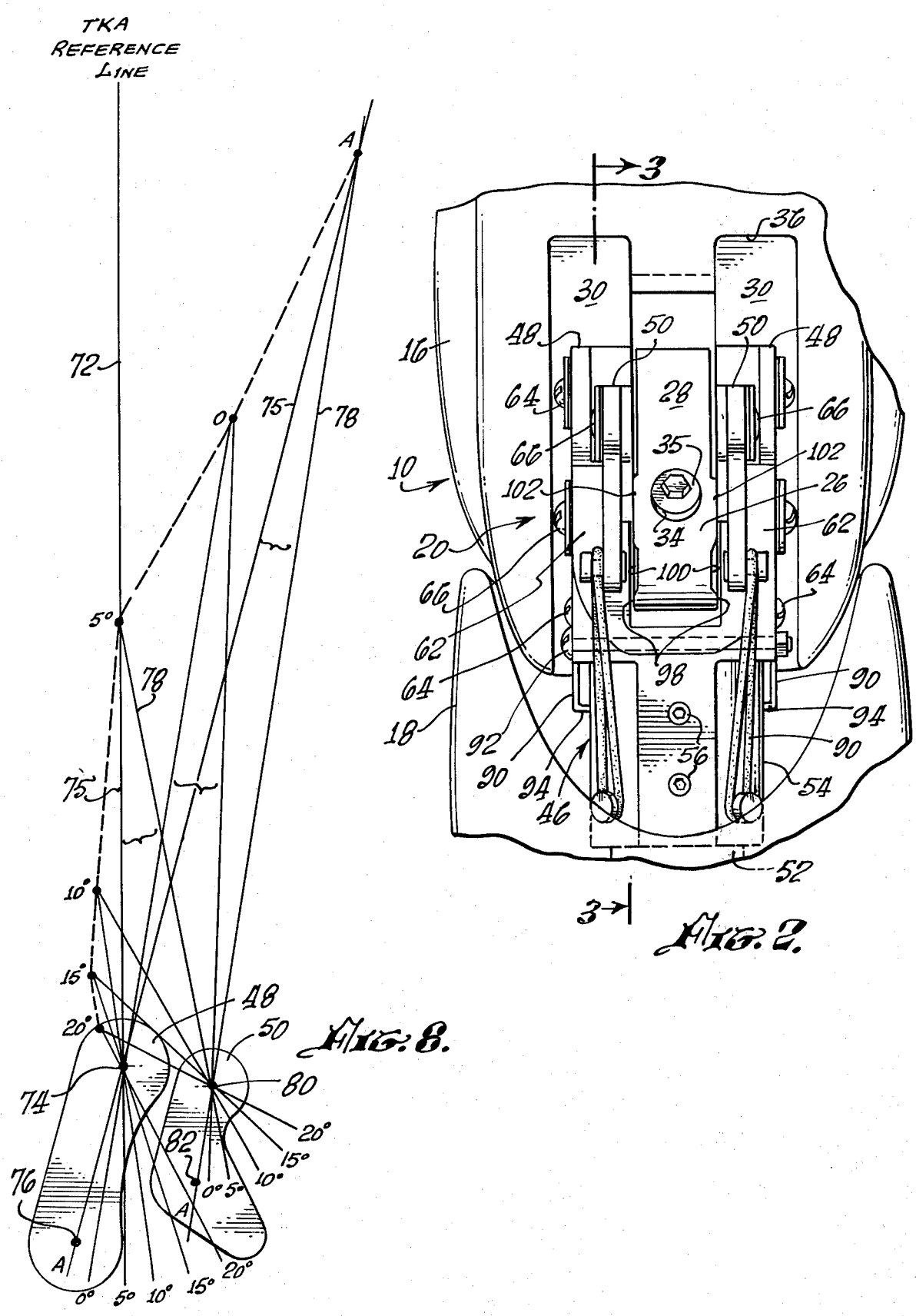

ARTIFICIAL POLYCENTRIC KNEE JOINT

BACKGROUND OF THE INVENTION

1. Field of the Invention

This invention relates generally to the art of leg prosthesis and, more particularly, to a prosthetic knee joint having a four-bar linkage system.

2. Description of the Prior Art

As is well known in the art, several problems and difficulties are encountered in providing a desirable artificial knee joint that is capable of geniculating in a manner similar to the human knee.

Considerable study and effort have been directed to improvement in leg prosthesis, especially as it relates to knee joints in artificial legs for the severely handicapped amputees.

The knee joint in a standard artificial limb is traditionally of the single-axis type which, in the past, has provided an acceptable function for many amputees. In this design, knee stability during weight-bearing is achieved by positioning the knee axis in such a way, relative to the body-weight action line, that the knee can be extended. In addition, a movement from active hip-extension muscles is required during the weight-bearing phase of the walking cycle. This means that the amputee must walk during weight-bearing over a fully extended knee, which is physiologically abnormal and contributes to the unnatural appearing gait of the "above-knee" amputees. Furthermore, when amputations are performed through the knee joint, the resulting long stump leaves insufficient space for the single-axis knee mechanism. In this case, single-axis side joints are required, resulting in greater fabrication time and an unpleasant appearance of the finished device due to excessive width of the knee.

These and other shortcomings of the single-axis design have encouraged those knowledgeable in the art to seek other mechanisms for knee devices.

Thus, the applicant herein discloses a four-bar linkage system, which yields polycentric (or many centered) action of the center of knee rotation.

SUMMARY OF THE INVENTION

The present invention comprises an artificial knee joint that includes therein a four-bar linkage mechanism. Accordingly, the knee joint is connected and interdisposed between the upper leg member, which will be referred to as the socket that receives the amputee's stump therein, and the lower limb which will be referred to as the shank of the prosthesis.

The artificial knee joint comprises a knee mounting block secured directly to the terminating end of the socket member forming a fixed linkage thereto. The lower shank member generally includes a mounting shaft fixedly secured therein having an extended portion to receive the second substantially fixed linkage-support member.

Interconnecting the mounting block and the linkage-support member are at least two rotatable linkage bars, wherein the bars are arranged in pairs to be oppositely arranged on each side of the knee block. Thus, to provide the proper biasing force to the movement of the shank with respect to the knee joint there is included a biasing member attached between one of the linkage bars and the linkage-support member.

In order to prevent uncontrolled movement during the swinging motion of the shank portion of the prosthesis, there is included a braking device, which is adjustable to regulate or impede, to a degree, the action of the forces of inertia during the swing phase of the amputee's gait. Also provided therein is a shock absorber positioned to engage a linkage bar whereby, when the shank returns to a normal vertical alignment with the socket member at the termination of the swing phase, the forces impacted thereby are received and cushioned by the shock absorbing device. The shock absorbing device is also adapted to be movable so as to contact the linkage bar at a pre-determined point whereby the stabilizing point of the center of gravity of the prosthesis can be regulated, depending upon the intrinsic energy of the amputee to which the device is fitted.

OBJECTS AND ADVANTAGES OF THE INVENTION

The present invention has for an important object a provision wherein an artificial knee joint comprises a four-bar linkage arrangement, thereby allowing greater stability of the entire leg prosthesis, in both stance and swing phases, during ambulation.

It is another object of the invention to provide an artificial knee joint that allows knee stability at heel strike and ease of flexion before swing through.

It is still another object of the invention to provide a prosthetic knee device that is so arranged as to give a motion somewhat similar to a normal knee, thereby contributing to a natural appearing gait of the knee amputee.

It is a further object of the present invention to provide an artificial knee joint wherein the polycentric linkage will enable a prosthetic toe to clear ground level during ambulation and allow the amputee to place his heel against any uneven base, without the fear of having the leg folding under him. Thus, the amputee can easily walk down as well as up a ramp or stairs.

It is still a further object of the invention to provide a device of this character whereby linkage bars are so arranged as to make a compact unit, wherein the overall size and design lends itself to a better cosmetic appearance—which heretofore has been lacking in this area of prosthesis.

Still another object of the invention is to provide a device of this character that gives a substantially normal gait by incorporating a braking unit to control the flexion of the shank portion of the leg member.

It is still another object of the invention to provide a prosthetic knee joint that is simple in design and rugged in construction.

A still further object of the invention is to provide a device of this character that includes a means whereby the knee center can be adjusted according to the particular patient's intrinsic energy.

And still another important object of the invention is to provide a device of this character that is easy to service and maintain.

The characteristics and advantages of the invention are further sufficiently referred to in connection with the accompanying drawings, which represent one embodiment. After considering this example, skilled persons will understand that variations may be made without departing from the principles disclosed and I contemplate the employment of any structures, arrangements or modes of operation that are properly within the scope of the appended claims.

DESCRIPTION OF THE DRAWINGS

Referring more particularly to the accompanying drawings, which are for illustrative purposes only:

FIG. 2 is an enlarged rear-elevational view of the present invention seen from arrows 2—2 of FIG. 1 as being disposed within the knee joint area of the artificial leg;

FIG. 8 is a diagrammatic representation of the projected knee center and its various respective positions during flexion of the knee.

DESCRIPTION OF THE PREFERRED EMBODIMENT

Figure 1:
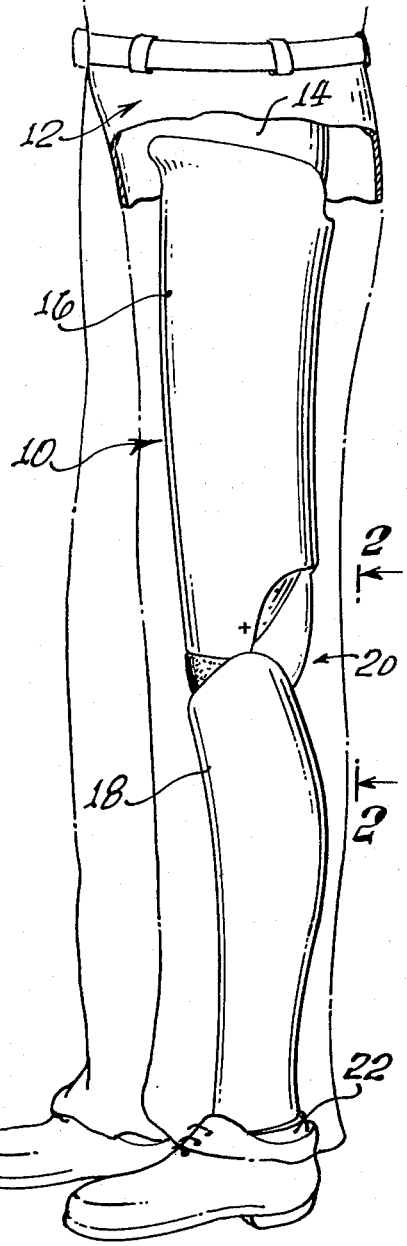
FIG. 1 is an illustration of the lower portion of a human body, wherein a leg prosthesis is secured to an above-knee stump having the present invention arranged in the knee joint thereof.

Referring more particularly to FIG. 1, there is shown an entire leg prosthesis, generally indicated at 10, attached to a human body 12, said body being shown as the lower half thereof. As can be seen, stump member 14 is of the type known as an "above-knee stump" to which is mounted the stump-receiving socket member 16. The lower portion of the artificial leg represents the shank member 18. Interconnecting each leg member is the present invention, referred to as a "prosthetic knee joint", generally designated at 20.

Secured to terminating end of the shank member 18 is a foot member 22, the construction and design of the present prosthesic knee joint 20 allowing for any well-known type of foot compatible for use therewith.

During the following description the terms "stance phase" and "swing phase" will be used. Therefore, there should be a general understanding of these terms. First, the stance phase is that phase of ambulation of an amputee, wherein the leg prosthesis makes contact with the floor and the entire body weight is applied thereto. The phase includes "heel-strike"; "mid-stance" (the leg being substantially vertical); and "push-off". At push-off the weight is shifted to the amputee's good leg, thereby allowing the "swing phase" to occur; that is, the shank geniculates rearwardly (acceleration), the toe rises above the floor level and proceeds to swing forward in a normal walking gait (swing-through). From this point the swing phase ends, when the leg prosthesis is fully extended in a forward manner just prior to the shifting of the body weight thereto.

As previously mentioned, considerable study and work has been directed to provide an artificial limb for above-knee amputees wherein not only stability is provided; but, in addition, a normal natural gait can be simply accomplished. Hence, through the implementation of the present invention the above is now practical.

Figures 3, 4, 7:
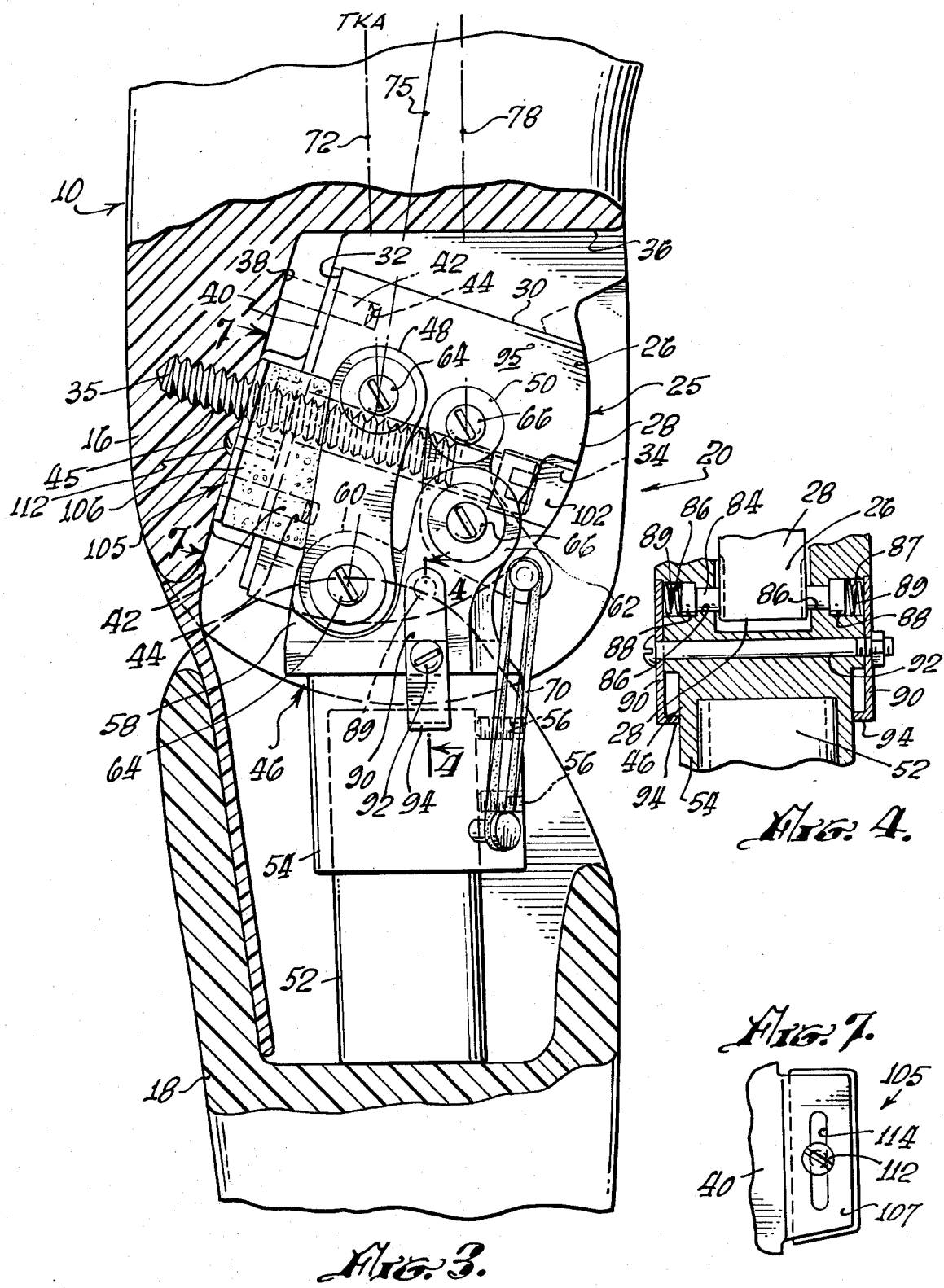
FIG. 3 is a cross-sectional view taken substantially along line 3—3 of FIG. 2 thereof.
FIG. 4 is a cross-sectional view of the braking unit taken substantially along line 4—4 of FIG. 3 thereof.
FIG. 7 is a view taken along line 7—7 of FIG. 3, wherein the means for adjusting the shock absorber is shown.

Referring now to FIGS. 2 and 3, there is shown an artificial polycentric knee joint, otherwise known as a four-bar linkage knee, generally indicated at 25, comprising a main mounting block 26 that is secured to the distal end of the socket 16. Said mounting block 26 is clearly shown in FIG. 5 as having a portion thereof formed with an arcuate side wall 28, an upper flat side 30, and a rear flat side wall 32.

A bore 34 is disposed longitudinally through the block 26; that is, the bore 34 extends from the arcuate side wall 28 to the rear flat side wall 32, through which a bolt 35 passes. Thus, the distal end of the socket 16 is arranged with a recessed compartment 36 to fixedly recess the block 26, which at this time would represent a skin member.

Mounted between wall 38 of the recess 36 and the block 26 is an alignment plate 40 having outwardly extending aligning pins 42, said pins being arranged to be received within openings 44 disposed in rear wall 32, as seen in FIG. 3. Thus, bolt 35 passes through bore 34, through plate 40, and is then threadably received in socket member 16 at point 45. In essence then, block 26 represents one of the linkage bars under the four-bar system.

Figure 6:
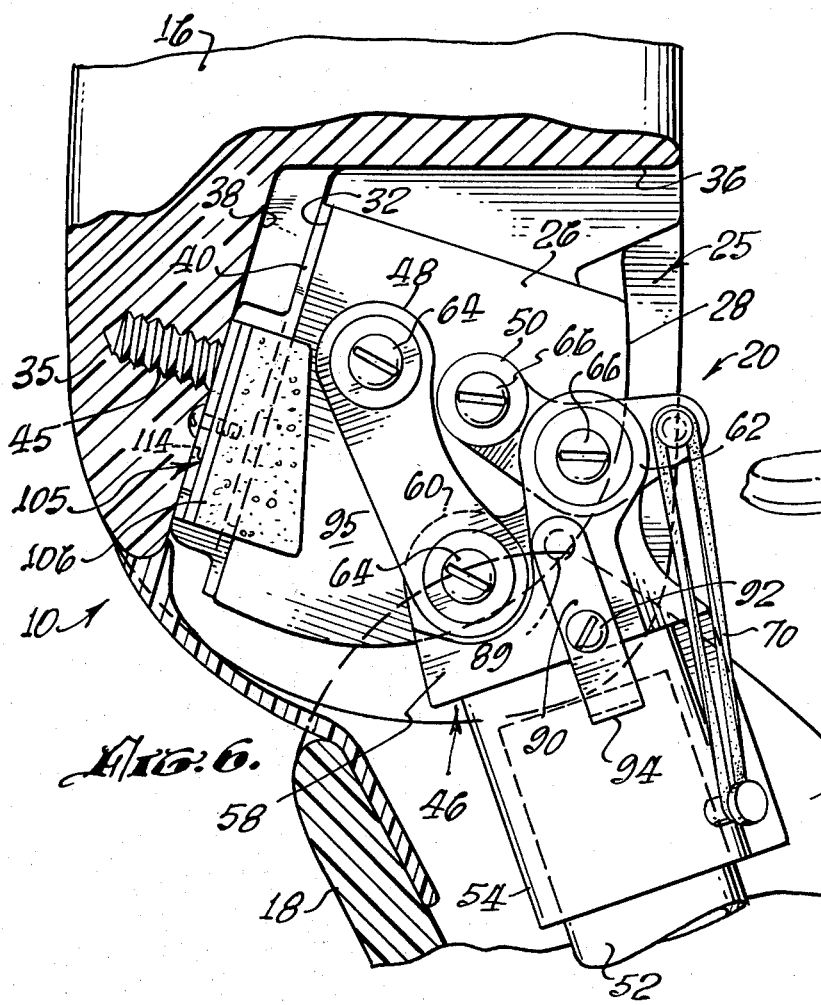
FIG. 6 is a similar cross-sectional view to that of FIG. 3 wherein the knee joint is shown in a geniculated position.

The second member representing another linkage bar is the linkage-support carriage member, indicated generally at 46. This carriage member is interconnected to the mounting block 26 by two juxtapositioned linkage bars 48 and 50, respectively, linkage bars 48 and 50 being arranged in pairs and positioned on opposite sides of the mounting block 26 and support carriage 46, as illustrated in FIG. 2. The support carriage is so arranged as to be removably mounted to shank 18, which is provided with a center-support strut 52. Hence, the carriage comprises a lower neck portion 54 adapted to removably receive strut 52 therein. Means for removably securing said carriage to said strut 52 is provided by set screws 56. Integrally formed to the lower neck portion 54 is a mounting head 58 formed in a substantially "U"-shaped fashion, wherein block 26 is allowed to pass therethrough when the knee joint is activated, as shown in FIG. 6. The head is so arranged as to include a pair of mounting ears 60 and 62 to which linkage bars 48 and 50 are respectively secured. From ear 60 linkage bar 48 extends upwardly and is secured to block 26 by securing means, such as bolts 64, which is also used to connect said linkage 48 to ear 60. The adjacent linkage bar 50 is secured to ear 62 by bolt 66, the bar 50 extending upwardly and being attached to block 26 by a second bolt 66. Thus, a four-bar linkage is formed between the four members—the block 26, the carriage 46, and the first and second linkage bars 48 and 50.

Accordingly, the arrangement of elements of the four-bar linkage system provides a prosthetic knee that is instantly stable during weight-bearing; that is, the arrangement herein allows the axis of the knee to be located behind the load line from the greater trochanter of the femur to the point of loading at the ankle, the approximate coronal plane in which body-weight is transferred to the limb. Furthermore, it allows the amputee to be able to control the knee—that is, for him to be able to land on a flexed knee and still be able to control knee flexion by applying an extension movement with his hip exterior muscles during stance phase. Thus, the knee axis should be located above the anatomical knee and posterior to the substantially vertical imaginary line, indicated as the TKA reference line seen in FIG. 8. A more detailed description of the relationship of the geniculation of the knee joint and the effective knee center with respect to the TKA line will be presented hereinafter.

Once the knee joint has been actuated, generally by the movement of the amputee's stump and related muscles, the components are caused to move to a point over the C G point and the flexion of the shank is aided by the biasing means 70, which is attached at one end to linkage bar 50 and the opposite end to the lower neck portion 54 of the carriage 46. The biasing means is shown as a flexible band, but it should be understood that various spring members can be used in place thereof. The linkage bar 50 is formed substantially like a well known bell crank. This flexion takes place during the swing phase and when an amputee attempts to sit down. During both situations, the knee is permitted to flex with ease in a very normal manner.

However, as previously stated, the knee must be controlled in a positive stable manner during stance phase, particularly when ambulation occurs during a non-level condition, such as walking down a ramp or stairs. This is accomplished by positioning an imaginary knee center above the artificial knee 25 and posterior to the TKA line. Thus, referring to FIG. 8, there is shown the vertical TKA reference line indicated at 72, wherein the line 72 extends downwardly through the center of the top pivot point 74 of linkage bar 48. To form the imaginary knee center, which in FIG. 8 is located at A, two additional imaginary lines are formed, one by projecting a line 75 through each pivot point 74 and 76, respectively, disposed in linkage bar 48, the other by projecting a line 78 through both pivot points 80 and 82 of linkage bar 50. When the linkage bars 48 and 50 are positioned as shown in FIG. 8, lines 75 and 78 intersect at A, thereby providing a posterior projected knee center. Thus, it can be seen from the diagram that the first 5° of movement will place the knee center directly in line with the TKA line 72. Hence, the center moves inwardly and downwardly, allowing ease of flexion once the center reaches line 72. At this position, pivot points 74 and 76 are substantially vertical and superpose over the TKA line 72, while line 78 intersects line 75 on the TKA line. Once the intersecting point of lines 75 and 78 pass forwardly of the TKA line, the knee flexion occurs much more rapidly. That is, shank 18 bends rearwardly with ease in a very normal manner relative to that of the human leg reaction. It should be kept in mind that pivot points 74 and 80 of respective links 48 and 50 remain stationary with respect to each other, each pivot point 74 and 80 being fixed to block 26; while pivot points 76 and 82 of respective linkage bars 48 and 50 are fixed to support-carriage member 46 and move therewith when flexion of the artificial knee occurs. Thus, the degree of the bending movement of the shank increases rapidly as it flexes rearwardly during ambulation.

However, during the return of the shank 18 to its extended position in the swing phase, the speed of forward travel impacted thereby is considerable and must be controlled. Therefore, there is included a braking means, which controls the flexion of the knee at various positions during the bending thereof. The braking means comprises a pair of braking shoes 84 which are arranged to be received in bores 86 oppositely disposed on both sides of the support carriage 46, as seen in FIG. 4. A contour base 87 is formed in bores 86 in which the enlarged heads 88 of shoes 84 are received, with biasing springs 89 positioned against each head 88. In order to provide the proper tension thereon and to secure each spring and brake pad in place, there is included an arm member 90 ajustably mounted to the support carriage by bolt and nut 92. The arms are formed with inwardly bent ears 94, whereby the arms 90 can be adjusted to apply varied pressures to springs 89, which in turn adjust the pressure of each pad against the side walls 95 of said mounting block 26. The braking means additionally includes a cam surface 96 formed along each leading edge of each surface 95, as seen in FIG. 5.

Figure 5:
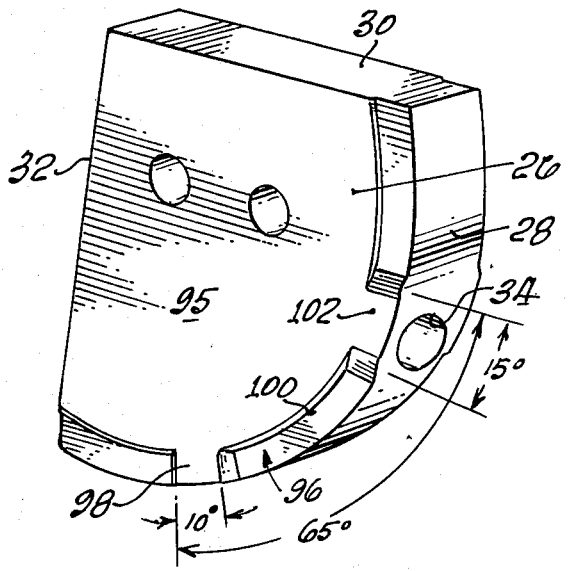
FIG. 5 is a perspective view of the knee block that forms one of the four linkage bars.

When the amputee's leg prosthesis is fully extended, the braking shoe 84 engages the raised area 98 of the cam surface 96 (See FIG. 5). Area 98 is approximately 10° wide which allows stability and flexion control by the movement of the amputee's stump and muscles. Following the raised area 98, there is a recessed area 100, which allows greater freedom in the bending movement, said recessed area 100 being approximately 40° in length. Thus, once the knee geniculates past the 10° point, as seen in chart of FIG. 8, the shank will fold rearwardly in a normal manner. The generally complete flexion of the shank is approximately 65° and, therefore, the last 15° thereof is again raised as at 102. As the braking shoe reaches this point, the shank is slowed and then stopped for its return swing, which is called "swing-through".

Accordingly, the braking means continuously engages and disengages during the swing-phase of ambulation. It is important to note that, when the leg agains reaches its fully extended position, the deceleration phase begins. There is created a terminal impact by the moving force of the shank against the socket 16. However, to prevent this impact, there is provided a shock absorbing means, generally indicated at 105, which comprises a resilient shock pad 106 adjustably mounted to flange member 107 of bracket 40. A pair of pads 106 are located on each side of the knee structure and is arranged to be directly engaged by each linkage arm 48. Thus, as the knee joint reaches the position wherein the artificial leg is fully extended, the links 48 contact the respective resilient pads, thereby dissipating the force of impact. Hence, the amputee does not feel a jolt through his stump whenever the leg is fully extended during ambulation.

In addition, the shock pad 106 provides an adjusting means whereby the position thereof in a vertical plan controls the angle of the linkages 48 and 50. The adjusting of pad 106 regulates the position at which linkage arm 48 will engage the converging walls of pad 106. That is, pivot points 74, 76, 80 and 82 are adjustable in relationship to one another, thereby allowing for the adjustment of the projected knee center A. Therefore, by positioning pad 106 by means of screw 112, which is received through a vertical slot 114 of flange 107, the intersecting lines 75 and 78 can be changed to move the projected center line with respect to the TKA line 72.

The placement of the projected knee center depends on the individual amputee, as the position of the projected knee center dictates the amount of forces required by the amputee to start the geniculation of the prosthesis knee joint. Thus, the stability of the leg is regulated by the position of the pads 106.

Once, the projected knee center passes the TKA line, the weight of the amputee will flex the artificial leg in a normal manner, then shifting his weight to the good leg.

The invention and its attendant advantages will be understood from the foregoing description and it will be apparent that various changes may be made in the form, construction and arrangement of the parts of the invention without departing from the spirit and scope thereof or sacrificing its material advantages, the arrangement herein before described being merely by way of example, and I do not wish to be restricted to the specific form shown or uses mentioned, except as defined in the accompanying claims.

I claim:

1. An artificial polycentric knee-joint mechanism interconnecting an upper stump-receiving socket member and a lower swingable shank member defining a prosthetic leg member, wherein the knee joint comprises:
   a substantially stationary mounting block secured to the upper socket member, forming a transverse link member;
   a support carriage secured to the lower shank member, defining a second link member;
   pivot means interconnecting said mounting block to said support carriage comprising:
   a first substantially vertical linkage bar positioned forward on said block and said carriage;
   a second substantially vertical linkage bar juxtapositioned aft of said first linkage bar, allowing geniculation between the stump receiving socket and the swingable shank member;
   biasing means connected between said second linkage bar and said support carriage;
   braking means supported in said carriage for engagement with said mounting block, whereby the swing action of the shank member is controlled thereby; and
   shock absorbing means arranged to engage said first linkage bar when said shank member swingably returns to a fully extended position.

2. An artificial knee joint as recited in claim 1, wherein said first linkage bar includes a first pivot at the point of attachment to said mounting block, said first pivot being substantially fixed, and a second pivot at the point of attachment to said support carriage, said second pivot being movable relative to said first pivot of said first linkage bar; and wherein said second linkage bar includes a third pivot at the point of attachment to said mounting block, said pivot being substantially fixed, and a fourth pivot at the point of attachment to said support carriage, said fourth pivot being movable relative to said third pivot.

3. An artificial knee joint as recited in claim 2, wherein the alignment of said first and second pivots with respect to the alignment of said third and fourth pivots defines the position of a projected knee center arranged to be located posterior to the TKA line and substantially above the knee joint, where the TKA line represents the vertical center line of the upper socket and lower shank when forming a fully extended leg member.

4. An artificial knee joint as recited in claim 3, wherein said knee joint includes adjusting means to control the angular displacement of said pivots by adjustably engaging said first linkage bar.

5. An artificial knee joint as recited in claim 4, wherein said adjusting means comprises:
   a pad having a converging wall for engagement with said first linkage arm;
   a mounting bracket secured to said socket member arranged to movably receive said pad; and
   means for positioning said pad on said bracket in vertical alignment with said first linkage arm, thereby controlling the angular alignment of said pivots.

6. An artificial knee joint as recited in claim 5, wherein said braking means comprises:
   a cam surface formed on each side of said mounting block;
   a pair of brake shoes operably disposed in said supporting carriage and arranged for engagement with respective cam surfaces;
   mounting arms adjustably secured to said support carriage; and
   a spring disposed between said mounting arms and said brake shoes, causing braking engagement with said cam surfaces.

7. An artificial knee joint as recited in claim 6, wherein said braking means includes means for adjusting the force of said spring against said brake shoes.

8. An artificial knee joint as recited in claim 7, wherein said second linkage arm forms a bell crank, wherein one end thereof is connected to said biasing means to control the flexion between said socket and said shank member.

9. An artificial knee joint as recited in claim 8, wherein said knee joint includes an alignment plate secured to said socket and having outwardly extending alignment pins positioned to be received in respective alignment holes disposed in said mounting block; and wherein said mounting block includes a central longitudinal bore and a bolt removably received therethrough for attachment to said socket.

10. An artificial knee joint as recited in claim 7, wherein said cam surfaces comprises:
    a plurality of raised surfaces; and
    a plurality of recessed surfaces, wherein the first raised area defines a 10° braking surface, and the second raised area defines a 15° braking surface, having a 40° recess interdisposed therebetween.

* * * * *